(12) United States Patent
Ng et al.

(10) Patent No.: US 7,334,458 B2
(45) Date of Patent: Feb. 26, 2008

(54) DIRECT METHOD TO DETERMINE PARTICULATE CONCENTRATION IN A DISPERSION

(75) Inventors: Bryan Ng, Ithaca, NY (US); Cindy C. Chen, Rochester, NY (US); Lanhui Zhang, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 111 days.

(21) Appl. No.: 11/206,783

(22) Filed: Aug. 19, 2005

(65) Prior Publication Data

US 2007/0056359 A1    Mar. 15, 2007

(51) Int. Cl.
*G01N 33/00* (2006.01)
(52) U.S. Cl. .................................... 73/61.41
(58) Field of Classification Search ................ 34/314; 73/61.41
See application file for complete search history.

(56) References Cited

U.S. PATENT DOCUMENTS

| | | | |
|---|---|---|---|
| 3,481,865 A * | 12/1969 | Samuels, Jr. ............ 208/251 R |
| 4,233,384 A | 11/1980 | Turner et al. |
| 4,265,990 A | 5/1981 | Stolka et al. |
| 4,299,897 A | 11/1981 | Stolka et al. |
| 4,306,008 A | 12/1981 | Pai et al. |
| 4,439,507 A | 3/1984 | Pan et al. |
| 4,965,162 A * | 10/1990 | Aonuma et al. ......... 430/108.6 |
| 5,096,795 A | 3/1992 | Yu |
| 5,725,983 A | 3/1998 | Yu |
| 5,802,442 A * | 9/1998 | Konno et al. .............. 399/308 |
| 6,143,675 A * | 11/2000 | McCollam et al. ........ 442/221 |
| 6,228,551 B1 * | 5/2001 | Ohmura et al. ........ 430/108.21 |
| 6,303,254 B1 | 10/2001 | Yu et al. |
| 6,326,111 B1 | 12/2001 | Chambers et al. |
| 6,337,166 B1 | 1/2002 | Chambers et al. |
| 6,696,214 B2 * | 2/2004 | Katayama et al. .......... 430/131 |
| 6,881,784 B2 * | 4/2005 | Cody et al. ................ 524/794 |
| 2005/0100806 A1 * | 5/2005 | Hongo et al. ............... 430/78 |

* cited by examiner

*Primary Examiner*—Michael Cygan
(74) *Attorney, Agent, or Firm*—Oliff & Berridge, PLC

(57) ABSTRACT

Particulate material concentration of a dispersion is detected by providing a known amount of dispersion including particulate material, a solvent, and other optional components; centrifuging the dispersion and separating the particulate material from the dispersion; drying the particulate material; and weighing the particulate material to determine a particulate material concentration of the dispersion.

5 Claims, No Drawings

US 7,334,458 B2

DIRECT METHOD TO DETERMINE PARTICULATE CONCENTRATION IN A DISPERSION

BACKGROUND

The disclosure relates to novel methods for determining polytetrafluoroethylene (PTFE) or other filler or particulate concentration in dispersions, such as dispersions used in the manufacture of electrophotographic devices. More in particular, the disclosure relates to novel methods of determining the PTFE or other filler or particulate concentration of charge transport layer (CTL) and anti-curl back coating (ACBC) layer dispersions using centrifugation and drying methods.

In the art of electrophotography, an electrophotographic device comprising a photoconductive insulating layer on a conductive layer is imaged by first uniformly electrostatically charging the surface of the photoconductive insulating layer. The device is then exposed to a pattern of activating electromagnetic radiation such as light, which selectively dissipates the charge in the illuminated areas of the photoconductive insulating layer while leaving behind an electrostatic latent image in the non-illuminated areas. This electrostatic latent image may then be developed to form a visible image by depositing finely divided electroscopic toner particles, for example from a developer composition, on the surface of the photoconductive insulating layer. The resulting visible toner image can be transferred to a suitable receiving member such as paper.

Electrophotographic imaging members are usually multilayered photoreceptors. U.S. Pat. No. 5,725,983, incorporated herein by reference in its entirety, describes an electrophotographic imaging member including a supporting substrate having an electrically conductive layer, a hole blocking layer, an optional adhesive layer, a charge generating layer, a charge transport layer, a ground strip layer and an optional overcoating layer, at least one of the charge transport layer, ground strip layer and the overcoating layer comprising a blend of inorganic and organic particles homogeneously distributed in a film forming matrix, the inorganic particles and organic particles having a particle diameter less than about 4.5 micrometers. These electrophotographic imaging members may have a flexible belt form or rigid drum configuration. For most multilayered flexible photoreceptor belts, an anti-curl layer is usually employed on the back side of the substrate support, opposite to the side carrying the electrically active layers, to achieve the desired photoreceptor flatness.

Examples of photosensitive members having at least a separate charge generation layer (CGL) and charge transport layer are disclosed in U.S. Pat. Nos. 4,265,990, 4,233,384, 4,306,008, 4,299,897 and 4,439,507. The disclosures of these patents are incorporated herein in their entirety. The charge generating layer is capable of photogenerating holes and injecting the photogenerated holes into the charge transport layer. This photogenerating layer includes, for example, inorganic photoconductive particles or organic photoconductive particles dispersed in a film forming polymeric binder.

The charge transport layer generally includes at least one charge transport material. Any suitable charge transport molecule known in the art may be used, and the charge transport molecules may either be dispersed in the polymer binder or incorporated into the chain of the polymer. Preferably, the charge transport material comprises an aromatic amine compound. More preferably, the charge transport layer comprises an arylamine small molecule dissolved or molecularly dispersed in the binder. Typical aromatic amine compounds include triphenyl amines, bis and poly triarylamines, bis arylamine ethers, bis alkyl-arylamines and the like. U.S. Pat. No. 6,337,166, incorporated herein by reference in its entirety, describes suitable binders including polycarbonates, polyesters, including polyethylene terephthalate, polyurethanes, polystyrenes, polybutadienes, polysulfones, polyarylethers, polyarylsulfones, polyethersulfones, polycarbonates, polyethylenes, polypropylenes, polymethylpentenes, polyphenylene sulfides, polyvinyl acetates, polyvinylbutyrals, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, polyvinylchlorides, polyvinyl alcohols, poly-N-vinylpyrrolidinone)s, vinylchloride and vinyl acetate copolymers, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazoles, and the like. These polymers may be block, random or alternating copolymers. Additional additives, such as antioxidants or leveling agents, may be included in the charge transport layer material as needed or desired. The solvent system comprises of at least tetrahydrofuran (THF). Other or alternative solvents may also be present, if desired.

Conventional charge transport layers without additives suffer from a fast, nearly catastrophic wear rate of 8 to 10 microns or more per 100 kilocycles when the photoreceptor is charged using an AC bias charging roll (BCR). The use of AC bias charging rolls to charge a photoreceptor surface is conventional in the art for forming images in low speed, for example up to 40 ppm, imaging devices (e.g., copiers and printers). However, the corona generated from the AC current, applied to the BCR, decomposes on the top photoreceptor layer. The decomposed material can be easily removed by a cleaning blade. Such a repeated process during the printing cycle wears out the photoreceptor top layer very quickly.

Wear rate is a significant property in that it limits the life of the photoreceptor, and photoreceptor replacement in electrostatographic devices such as copiers and printers is very expensive. It is thus very significant to limit wear of the photoreceptor so as to achieve a long life photoreceptor, particularly with respect to small diameter organic photoreceptor drums typically used in low speed copiers and printers that are charged with an AC BCR. In such small diameter drums, 100 kilocycles translates into as few as 10,000 prints. CTL wear results in a considerable reduction in device sensitivity, which is a major problem in office copiers and printers that typically do not employ exposure control. In addition, the rapid wear of the top photoreceptor layer requires better cleaning of the debris from the photoreceptor surface in order to maintain good toner transfer and good copy quality.

U.S. Pat. No. 5,096,795, incorporated herein by reference in its entirety, describes an electrophotographic imaging member comprising a charge transport layer comprised of a thermoplastic film forming binder, aromatic amine charge transport molecules and a homogeneous dispersion of at least one of organic and inorganic particles having a particle diameter less than about 4.5 micrometers, the particles comprising a material selected from the group consisting of microcrystalline silica, ground glass, synthetic glass spheres, diamond, corundum, topaz, polytetrafluoroethylene, and waxy polyethylene, wherein said particles do not decrease the optical transmittancy or photoelectric functioning of the layer. The particles provide coefficient of surface contact friction reduction, increased wear resistance, and durability against tensile cracking without adversely affecting the optical and electrical properties of the imaging member.

Thus, it has been broadly known to attempt to utilize small particles such as polytetrafluoroethylene (PTFE) in outer layers of a photoreceptor in an effort to increase the cleanability and durability of the outer photoreceptor layers. PTFE particles may be incorporated into the dispersion along with a surfactant. Any commercially available PTFE particle may be employed, including, for example, MP1100 and MP1500 from Dupont Chemical and L2 and L4, Luboron from Daikin Industry Ltd., Japan. The size of the PTFE particles are preferably less than 2 micron diameter, most preferably less than 0.3 micron. Preferably, the surfactant is a fluorine-containing polymeric surfactant. Most preferably, the fluorine-containing polymeric surfactant is a fluorine graft copolymer, for example GF-300 available from Daikin Industries. These types of fluorine-containing polymeric surfactants are described in, for example, U.S. Pat. No. 5,637,142, incorporated herein by reference in its entirety.

Filler or particulate materials, such as PTFE, are also known to be used in other layers of a photoreceptor, including in an anti-curl backing layer and/or in a ground strip layer. For example, U.S. Pat. No. 6,303,254 describes an electrostatographic imaging member including: a flexible supporting substrate; an imaging layer having an optional adjacent ground strip layer coated on one side of the substrate; and an anti-curl backing layer coated on the other side of the substrate which layer is comprised of a film forming polymer binder, an optional adhesion promoting polymer, and a dispersion of polytetrafluoroethylene particles which dispersion has particles with a narrow diameter particle size distribution of from about 0.19 micrometer to about 0.21 micrometer, and an average diameter particle size of about 0.20 micrometer. The optional ground strip layer can include the same dispersion of polytetrafluoroethylene particles as the anti-curl backing layer.

Particles such as polytetrafluoroethylene tend to aggregate and/or slowly settle over time in a CTL coating dispersion as a result of the inherent instabilities of current formulations and the inadequacy of the surfactants to completely stabilize the system. Thus, it is necessary to frequently stir the dispersion in order to avoid settling of the PTFE particles. Moreover, manufacturing processes involve the transport of the CTL through piping and filters that can unpredictably change the concentrations of PTFE.

Because reproducible thorough dispersion of PTFE can often prove difficult to obtain or maintain, it is important to accurately measure PTFE concentration regardless of particle size or uniformity of dispersion. In this regard, various methods to measure PTFE concentration exist. These methods include Differential Scanning Calorimetry (DSC) and light scattering.

The DSC method provides quantitative measurements of instantaneous heat capacities. By correlating heat capacity to weight of a standard sample, a relative concentration measurement can be obtained for PTFE. The shortcomings of this method are that DSC is sensitive to crystallinity and particle size. Theoretically, crystallinity can be accounted for only by specifically measuring each lot of PTFE for calibration. Moreover, DSC readings can also be affected by particle sizes and size distribution, thereby skewing heat capacity, and hence concentration, values. The magnitudes of these sources of error are unknown. This method continues to be a relatively expensive and time-consuming test to perform.

U.S. Pat. No. 6,326,111, incorporated herein by reference in its entirety, describe light scattering. In the light scattering method a small amount of the dispersion is added into a solvent mixture in a cell used for light scattering measurement. The solvent mixture has the same composition as the one used for dispersion. The solution is then mixed and sonicated to let the dispersion uniformly mix into the solvents. The cell is then put into the light scattering instrument for measurement. This measurement is strongly affected by particle sizes and particle size distributions. Even a few large particles in the testing material, such as from undermilling, aggregation or impurities, will dominate the scattering light signal. In principle, light scattering can be used to determine the PTFE concentration only if the unknown dispersion and all standard dispersions for the calibration curve are monodispersed with similar particle sizes and shapes, if the particle concentration is the only difference between the known dispersion and all standard dispersions for calibration (such as viscosity, temperature, refractive index) and if the concentrations of all dispersions are kept reasonably low to avoid multi-scattering.

These methods do not capture the complexity of PTFE-containing dispersions, which can have different distributions of particle size and can be non-uniform. In this regard, the utilization of the aforementioned methods involves the assumption that all of the solutions are uniform dispersions of single size particles.

This measurement problem becomes apparent in analyzing well-dispersed PTFE systems, with calibration to a poorly dispersed PTFE system. The usage of an original calibration curve developed with a series of dispersions of different particle size/distribution, coupled with a well-dispersed system of smaller particle size can cause DSC and light scattering techniques to register a much lower PTFE concentration than actuality.

One way to reduce the error is to generate unique calibration curves for each batch of dispersion to help account for PTFE lot and milling variations. However, this is impractical in practice. What is still desired, then, is a reliable method for measuring PTFE concentration regardless of uniformity of dispersion or particle size.

SUMMARY

It is therefore an object of the disclosure to provide a method to determine the PTFE or particulate concentration of dispersions, particularly dispersions used in forming photoreceptors, such as charge transport layer or anti-curl backing layer dispersions, accurately, without regard to particle size or uniformity of dispersion or the variation of crystallinity.

It is still a further object of the disclosure to provide a method to determine PTFE concentration of the total solid.

These and other objects are obtained by the present disclosure.

In a first aspect, the present disclosure relates to a method for detecting particulate material concentration of a dispersion comprising providing a known amount of dispersion comprising particulate material, a solvent, and other optional components; centrifuging the dispersion and separating the particulate material from the dispersion; drying the particulate material; and weighing the particulate material to determine a particulate material concentration of the dispersion.

In a further aspect, the present disclosure relates to a method of detecting particulate material concentration of a dispersion total solid comprising providing a known amount of dispersion comprising particulate material, a solvent, and other optional components; evaporating solvent of the dispersion; and weighing resultant solid to determine total solid percentage and particulate material concentration of total solid.

In a still further aspect, the present disclosure relates to a method for detecting the PTFE concentration of a photoreceptor layer forming dispersion comprising providing a known amount of dispersion comprising polymer binder, solvent, and PTFE particles; optionally diluting the dispersion; centrifuging the dispersion to provide a sediment comprising said PTFE particles and a supernatant; removing the resultant supernatant; adding additional diluent to the sediment; redispersing the resultant sediment in the diluent; drying the sediment; and weighing the dried sediment to determine PTFE concentration of the dispersion.

DETAILED DESCRIPTION OF EMBODIMENTS

The present disclosure addresses these and other needs by providing improved measurement methods. More particularly, the present disclosure provides methods for more accurately measuring the concentration of filler or particulate materials, such as PTFE, in dispersion systems. Such dispersion systems can be, for example, coating dispersions used in forming any of the various layers of a photoreceptor, such as the anti-curl back coating layer, the ground strip, the charge generating layer, the charge transport layer, an overcoat layer, and the like. The filler or particulate contained in the coating dispersion can be any particulate material that is not soluble in but is dispersed in the solvent, such that the particulate can be removed from the solvent by appropriate centrifuge techniques as described herein.

For example, the coating dispersion can be any suitable coating dispersion used for forming any of the above layers of a photoreceptor. Thus, one embodiment, the coating dispersion can be an anti-curl back coating layer dispersion containing a film-forming polymer, an optional adhesion promoting polymer, and particulate material such as polytetrafluoroethylene particles, dispersed in a suitable solvent. In another embodiment, the coating dispersion can be a charge transport layer dispersion containing a film-forming polymer, charge transport molecules, and particulate material such as polytetrafluoroethylene particles, dispersed in a suitable solvent. In a still other embodiment, the coating dispersion can be a charge generating layer dispersion containing a film-forming polymer and organic or inorganic photoconductive particles, dispersed in a suitable solvent. Other embodiments are directed to ground strip or overcoat layer coating dispersions, which dispersions can also contain a particulate material, an optional film-forming polymer, and other optional materials, dispersed in a suitable solvent.

In addition to PTFE particles, the measurement methods of the present disclosure can be used to measure other particulate material concentrations in coating dispersions. For example, the particulate material is not limited to PTFE, but instead can be any particulate material include other halogenated such as fluorinated polymer particles, such as ethylene-chlorotrifluoroethylene copolymer (ECTFE), ethylene-tetrafluoroethylene (ETFE), tetrafluoroethylene (TFE), polytetrafluoroethylene (PTFE), polytetrafluoroethylene fluorinated ethylene propylene (PTFE-FEP), polytetrafluoroethylene perfluoroalkoxy (PTFE-PFA), polyvinylidene fluoride (PVDF), and the like; metal oxide particles, such as aluminum oxide, iron oxide, titanium oxide, zirconium oxide, zinc oxide, and the like; silica particles; organic or inorganic pigment particles; and the like. In embodiments, the particulate material can be dispersed in a suitable solvent for forming the coating dispersion, but is not completely soluble in the solvent, so that the particulate material can be separated from the solvent and/or other components of the dispersion by centrifuge.

In embodiments, the particulate material can be dispersed in any suitable solvent or mixture of solvents, appropriate for the particular coating dispersion and its intended use. For example, typical solvents used for forming charge transport layer coating dispersions include methylene chloride, chlorobenzene, tetrahydrofuran, toluene, and the like; typical solvents used for forming overcoating layer coating dispersions include butanol, ethanol, methanol, and the like; typical solvents used for forming charge generating layer coating dispersions include alcohols such as methanol, ethanol and isopropanol, ketones such as acetone, methylethyl ketone and cyclohexanone, amides such as N,N-dimethyl formamide and N,N-dimethyl acetamide, sulfoxides such as dimethyl sulfoxide, ethers such as tetrahydrofuran, dioxane and ethylene glycol monomethyl ether, esters such as methyl acetate and ethyl acetate, cyclic hydrocarbons, aliphatic halogen hydrocarbons such as chloroform, methylene chloride, dichloroethylene, carbon tetrachloride and trichloroethylene, aromatic compounds such as benzene, toluene, xylene, ligroin, monochlorobenzene and dichlorobenzene, and the like. Of course, other solvents can be used in various coating dispersions, as desired.

Thus, while the following discussion may focus on the particulate filler being PTFE particles dispersed in a solvent and polymer binder to form a charge transport layer coating solution, the present disclosure is not limited to such embodiments, but can instead be applied to any such particulate materials in any such coating dispersions. The discussion of PTFE particles dispersed in a solvent and polymer binder to form a charge transport layer coating solution is exemplary only and illustrates only one embodiment of the invention.

The method proposed for PTFE concentration measurement is a direct measurement of PTFE mass after centrifugation and drying to isolate PTFE from other solids and solvents in the dispersion. Since binder polymer and other small molecules (e.g. charge transporting materials, surfactants, etc.) are soluble in solvent, they will stay in the solution and can be removed in a supernatant after centrifugation, while the PTFE particles to be measured are not soluble in the solvent, and thus will form a sediment during centrifugation. In embodiments, repeated dilution and centrifugation cycles help to ensure most of the binder and charge transporting materials are removed, as well as make centrifugation more efficient. The residual solvents are then evaporated during drying. Once centrifugation and drying are complete, only PTFE and a negligible amount of residual surfactants remain. As such, the PTFE can then be isolated and dried/baked to determine its weight with respect to the overall amount of dispersion originally added. Solid % is measured by weighing a thin sample of the dispersion before and after drying/baking. PTFE concentration of total solid is then calculated by dividing PTFE concentration of dispersion by the total solid percentage.

In the present disclosure, a method for detecting additive concentration of charge transport layer dispersions comprises providing a known amount of charge transport solution; centrifuging the charge transport solution and separating the additive from the charge transport solution; and drying and weighing the sediment to determine said additive concentration of charge transport layer dispersions.

In embodiments, particulate concentration, such as PTFE concentration, can be measured by techniques that are independent of particle size and dispersion quality by using a direct measurement of particulate mass. This is generally accomplished by isolating the PTFE from the binder polymer and charge transporting materials by the repeated washing and centrifugation of a dilute system. The residual solvents left in the centrifuged PTFE cake can be easily removed by drying.

This is a viable method because the polymers and charge transport materials in the system are dissolved into the solvents (such as THF and toluene) and thus will not separate from the solvents during centrifugation. PTFE, however, is dispersed in the solvent and can centrifuge out of the solution. Although there may be amounts of surfactants that are also centrifuged out, the small amounts relative to PTFE make them negligible and do not adversely impact the results obtained by the method.

To make the centrifugation process more efficient, the sample of charge transport solution can be diluted with additional solvent, such as THF, to decrease the viscosity and hence the centrifugation time. Centrifugation can be repeated by removing the supernatant and re-dispersing the sediment into fresh solvent, such as THF. This washing allows for a more pure sample of PTFE to be obtained, and hence a more accurate result.

Additionally, flocculants, coagulants or destabilizers of PTFE particles may be employed to accelerate the centrifugation process, as long as the amounts are small, or these additional materials can be removed by further washing. Examples of these types of materials include, but are not limited to, solvents that change the stabilization properties of the PTFE surfactants such as toluene for charge transport layers, competing surfactants as silicone oils or excess GF300 in Makrolon containing systems. Such flocculants, coagulants or destabilizers can also be used where the particulate material is other than PTFE, and can be selected based on the particular components of the dispersion.

In embodiments, the centrifugation can be conducted a single time, or it can be repeated one or more times to provide the desired result. For example, the centrifugation can be repeated at least once if desired, with total centrifuging cycles being more than 1. If desired, the sediment can be re-dispersed in solvent between each cycle, between alternate cycles, or randomly between cycles as desired. However, such re-dispersion is not required in all embodiments, and can be omitted between some or all cycles, if desired.

In some embodiments, where the obtained sediment from a centrifuge cycle is re-dispersed in additional solvent, the formed solution or dispersion can be subjected to additional mixing to help form a more uniform solution or dispersion. For example, such mixing can be conducted by any suitable method such as shaking, stirring, sonication, or the like. Such mixing can be conducted in conjunction with each re-dispersion, or only with some re-dispersions, as desired.

Once the final desired sediment is obtained, and all desired centrifuge cycles have been completed, the sediment can optionally be dried to remove any residual solvent or volatile components. Such drying can be conducted, for example, in a heated oven, in a vacuum, or the like.

The PTFE concentration in the charge transport material solution can then be readily obtained by weighing the dried sediment and comparing the weight to the original amount of solution processed. In this regard, the PTFE concentration is calculated by dividing the weight of the dried sediment by the original solution weight.

PTFE concentration of total solid can be calculated by dividing PTFE concentration of dispersion by total solid concentration (total solid percentage).

The process does not require a lot of time, and can be used to analyze many samples at once. More importantly, the results from experiments performed thus far are repeatable within a very small margin of error and are believed to be much more accurate than current methods. The importance of an accurate gauge of these parameters has many implications. Amongst others, there will be no confusion when the PTFE concentration levels are unacceptably low when there is a good dispersion, and GF300/PTFE ratios can be adjusted more precisely—an important parameter in dispersion quality.

This method can be used to measure concentrations of other pigments in dispersions, such as $TiO_2$ in undercoating layer dispersions and charge generating materials in charge generating dispersions. Besides, this method can be used to measure the pigment or other particulate concentration in solid films by re-dissolving binders in appropriate solvents.

In a further embodiment, the disclosure provides a method for determining a concentration of the total soluble materials in the charge transport layer solution. This method generally comprises the steps of providing a known amount of charge transport layer dispersion, evaporating solvent and volatile components from the dispersion, weighing a resultant solid, and comparing the obtained weight to the known starting amount of charge transport layer dispersion and known PTFE and polymer binder concentrations, to determine the total solids percentage and the total soluble material percentage.

An example is set forth hereinbelow and is illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

Test tubes were pre-dried in an oven at 135° C. for 30 minutes and then stored in desiccators for ready use. The weight of an empty test tube was recorded at first. Then, the unknown sample was added to the test tube and weighed. The test tube was diluted with THF until approximately 90% full, capped and shook by hand until the solution appeared approximately uniform. The sample was centrifuged for 60 minutes at 5,000 rpm with an IEC HN-SII Centrifuge. The supernatant was removed and fresh THF was added until the test tube was half full. A sonication probe was well cleaned and used to re-disperse the sediment until the solution appeared uniform. As the test tube was being withdrawn from the probe, THF was poured onto it and into the test tube to collect any PTFE that may have collected on it. This was done until the test tube was once again approximately 90% full. The solution was shaken by hand until uniform and centrifuged for 30 minutes at 5,000 rpm. Again, the supernatant was removed, the sediment re-dispersed by the probe and diluted, and centrifuged. The supernatant was removed and the outside of the test tube was wiped in case there was any outside contamination. The test tube was baked in an oven at 135° C. for 60 minutes. The test tube with the dry sediment was then weighed. This weight was divided by the original solution weight to yield the PTFE concentration within dispersion.

The results are tabulated below:

|  | Trial 1 | Trial 2 | Trial 3 | Trial 4 | Trial 5 | Trial 6 |
|---|---|---|---|---|---|---|
| Empty Test Tube (g) | 7.9724 | 7.9644 | 8.015 | 7.9595 | 7.9335 | 7.9792 |
| Unknown CTL Sample (g) | 3.5069 | 3.512 | 4.0577 | 4.0268 | 4.4958 | 4.4972 |
| Tube with Dried Sediment (g) | 8.0195 | 8.0136 | 8.0706 | 8.0162 | 7.9992 | 8.045 |
| PTFE Concentration of dispersion (%) | 1.343 | 1.401 | 1.370 | 1.408 | 1.461 | 1.463 |
| PTFE Concentration of total solid (%) | 5.14 | 5.31 | 5.17 | 5.34 | 5.66 | 5.65 |

Average PTFE Concentration of total solid is 5.4% ± 0.2%

Example 2

Total solid % can easily be measured by drying/baking. It involves weighing a sample of CTL solution, letting the solvent evaporate, and then weighing the resultant solid. In order to ensure all of the solvent is removed from the system, the solution should only be a thin layer (typically on an aluminum drying pan) and then elevated in temperature past the boiling points of THF and toluene for a duration of time. Initial solution weighing inaccuracies due to solvent evaporation can be alleviated by first filling a disposable pipette with solution, weighing the pipette, depositing the thin layer of solution onto a drying pan, and then weighing the pipette to determine how much solution was deposited.

Aluminum drying pans were pre-dried in an oven at 135° C. for 30 minutes and then stored in desiccators for ready use. An aluminum drying pan was weighed. A thin layer of an unknown CTL solution was placed in the drying pan and quickly weighed. The pan was then placed in an oven at 135° C. for 60 minutes. The pan with its contents was weighed. The difference between this value and the drying pan is the solid weight, which was divided by the solution weight to yield the solid %.

The results are tabulated below.

|  | Trial 1 | Trial 2 | Trial 3 | Trial 4 | Trial 5 | Trial 6 |
|---|---|---|---|---|---|---|
| Empty Pan (g) | 0.9662 | 0.9658 | 0.9664 | 0.9669 | 0.9672 | 0.9646 |
| Unknown CTL Sample (g) | 3.9020 | 5.5680 | 4.8970 | 1.9450 | 1.6830 | 3.2560 |
| Pan with Solids (g) | 1.9863 | 2.4348 | 2.2629 | 1.4800 | 1.4015 | 1.8081 |
| Solid % | 26.2 | 26.4 | 26.5 | 26.4 | 25.8 | 25.9 |

Average Solid % is 26.2% ± 0.3%

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method for detecting the PTFE concentration of a photoreceptor layer forming dispersion comprising:

(a) providing a known amount of dispersion comprising polymer binder, solvent and PTFE particles;
(b) optionally diluting the dispersion;
(c) centrifuging the dispersion to provide a sediment comprising said PTFE particles and a supernatant;
(d) removing the resultant supernatant;
(e) at least once after (d), adding additional diluent to the sediment and redispersing the resultant sediment in the diluent;
(f) for each time (e) is conducted, repeating (c) and (d);
(g) following completion of a final (d), drying the sediment;
(h) weighing the dried sediment to determine PTFE concentration of the dispersion;
(i) after determining the PTFE concentration of the photoreceptor layer dispersion, adjusting the PTFE concentration in the photoreceptor layer dispersion; and
(j) applying the photoreceptor dispersion as a coating during the manufacture of a photoreceptor to form a charge transport layer or an anti-curl backing layer therein.

2. The method of claim 1, wherein the determination of the PTFE concentration of the dispersion is calculated by dividing the weight of the sediment with the weight of the known amount of dispersion.

3. The method of claim 1, wherein the diluent is tetrahydrofuran.

4. The method of claim 1, further comprising determining PTFE concentration of total solid percentage of the photoreceptor layer dispersion by:

providing a known amount of the photoreceptor layer dispersion;
evaporating the solvent; and
weighing resultant solid to determine total solid percentage of the photoreceptor layer dispersion, and dividing the PTFE concentration of the photoreceptor layer dispersion by the total solid percentage of the photoreceptor layer dispersion.

5. The method of claim 4, wherein the solvent is evaporated by heating the solution past the boiling point of the solvent for a duration of time.

* * * * *